United States Patent
Oude-Vrielink et al.

(10) Patent No.: US 12,171,519 B2
(45) Date of Patent: Dec. 24, 2024

(54) LAPAROSCOPIC INSTRUMENTS

(71) Applicant: IMPERIAL COLLEGE INNOVATIONS LIMITED, London (GB)

(72) Inventors: Timo Joric Oude-Vrielink, London (GB); Fernando Basilio Avila Rencoret, London (GB); George Mylonas, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 1063 days.

(21) Appl. No.: 17/050,575

(22) PCT Filed: Apr. 29, 2019

(86) PCT No.: PCT/GB2019/051178
§ 371 (c)(1),
(2) Date: Oct. 26, 2020

(87) PCT Pub. No.: WO2019/207322
PCT Pub. Date: Oct. 31, 2019

(65) Prior Publication Data
US 2021/0113286 A1 Apr. 22, 2021

(30) Foreign Application Priority Data
Apr. 27, 2018 (GB) .................................. 1806943

(51) Int. Cl.
*A61B 34/00* (2016.01)
*A61B 17/00* (2006.01)
(Continued)

(52) U.S. Cl.
CPC ........ *A61B 34/71* (2016.02); *A61B 17/00234* (2013.01); *A61B 17/3423* (2013.01);
(Continued)

(58) Field of Classification Search
CPC .............. A61B 34/71; A61B 17/00234; A61B 17/3423; A61B 34/76; A61B 2017/3425;
(Continued)

(56) References Cited

U.S. PATENT DOCUMENTS

| 9,044,210 B1 | 6/2015 | Hoyte et al. | |
| 2004/0138529 A1* | 7/2004 | Wiltshire | A61B 1/0055 600/144 |

(Continued)

FOREIGN PATENT DOCUMENTS

| EP | 2329787 A2 | 6/2011 |
| EP | 2329789 A1 | 6/2011 |

(Continued)

OTHER PUBLICATIONS

Office Action for Japanese Application No. 2021-508080 dated Apr. 18, 2023, with English translation, 5 pages.
(Continued)

*Primary Examiner* — Richard G Louis
(74) *Attorney, Agent, or Firm* — Wegman Hessler Valore

(57) ABSTRACT

A medical apparatus comprises an instrument channel arranged to be inserted into the body of a patient to enable a medical instrument to be inserted through the instrument channel into the body of the patient. It further comprises at least one support structure arranged to be located around the body of the patient, a plurality of guide ports each arranged to be inserted into the body of the patient, a plurality of control linkages each of which is at least partly supported on the at least one support structure, and a plurality of control actuators. Each of the control linkages may be arranged to extend through one of the guide ports, to be connected to the medical instrument, and to be moved by a respective one of the control actuators thereby to manipulate the medical instrument within the body of the patient.

18 Claims, 10 Drawing Sheets

(51) Int. Cl.
*A61B 17/34* (2006.01)
*A61B 90/00* (2016.01)

(52) U.S. Cl.
CPC ...... *A61B 34/76* (2016.02); *A61B 2017/3425* (2013.01); *A61B 2090/064* (2016.02); *A61B 2562/0219* (2013.01)

(58) Field of Classification Search
CPC ...... A61B 2090/064; A61B 2562/0219; A61B 2017/2906; A61B 17/3476; A61B 2017/00566; A61B 2034/304; A61B 2090/065; A61B 2017/00022; A61B 2017/00199; A61B 2017/00212; A61B 2017/00398
See application file for complete search history.

(56) References Cited

U.S. PATENT DOCUMENTS

| | | | |
|---|---|---|---|
| 2006/0161136 A1* | 7/2006 | Anderson | A61B 34/37 606/1 |
| 2009/0227843 A1* | 9/2009 | Smith | A61B 17/3423 600/201 |
| 2010/0076259 A1 | 3/2010 | Asada et al. | |
| 2011/0133040 A1 | 6/2011 | Viola et al. | |
| 2011/0137129 A1 | 6/2011 | Heinrich et al. | |
| 2012/0053402 A1 | 3/2012 | Conlon et al. | |
| 2013/0197535 A1 | 8/2013 | Okada | |

FOREIGN PATENT DOCUMENTS

| | | |
|---|---|---|
| EP | 2329789 A2 | 6/2011 |
| EP | 2467074 A2 | 6/2012 |
| EP | 2499998 A2 | 9/2012 |
| JP | 2009534158 A | 9/2009 |
| JP | 2011115582 A | 6/2011 |
| JP | 2011115591 A | 6/2011 |
| JP | 2011172787 A | 9/2011 |
| WO | 9743943 A1 | 11/1997 |
| WO | 2007127199 A1 | 11/2007 |
| WO | 2011060046 A2 | 5/2011 |
| WO | 2011060046 A3 | 5/2011 |
| WO | 2015036753 A1 | 3/2015 |

OTHER PUBLICATIONS

European Communication pursuant to Rule 164(2)(b) and Article 94(3) EPC for Application No. 19721367.1 dated Oct. 22, 2021, 8 pages long.

Search Report issued in Application No. GB1806943.5 dated Oct. 26, 2018; 7 pages.

International Search Report and Written Opinion issued for International Application No. PCT/GB2019/051178 dated Oct. 16, 2019; 15 pages.

* cited by examiner

LAPAROSCOPIC INSTRUMENTS

CROSS REFERENCE TO RELATED APPLICATIONS

This application is a national phase of International Patent Application No. PCT/GB2019/051178 filed Apr. 29, 2019, which claims the priority filing benefit of Great Britain Patent Application No. 1806943.5 filed Apr. 27, 2018, which are incorporated herein by reference in their entireties.

FIELD OF THE INVENTION

The present invention relates to laparoscopic surgery and investigation.

BACKGROUND TO THE INVENTION

Laparoscopy revolutionized surgery by reducing its invasiveness. Every day, worldwide, minimally invasive surgery is used from the simplest day-surgeries, up to complicated multi-stage cancer or transplant surgeries. Laparoscopy uses small incisions, ports and cameras to visualize, investigate, and operate inside the abdomen using long and rigid surgical instruments. Laparoscopy reduces the rate of complications, improves post-operative pain and shortens the recovery time, when compared to open surgery. However, laparoscopic instrument handling is challenging and counterintuitive when compared to open surgery, mainly because of the indirect visualization via a laparoscope, the pivoting of the instruments in the ports (fulcrum effect) and the lack of tactile (haptic) feedback. This added complexity explains its high dependence on the surgeons' experience, leading to a steep learning curve, and increased procedural times. While current commercially available robotic-assisted surgery (RAS) systems bring back intuitiveness to the instrument's handling, the adoption of RAS systems is limited because of their high capital cost, large footprint in the operating room and long setup times. Likewise, RAS is still not cost-effective when compared to conventional laparoscopy. RAS with all its benefits, such as immersive 3-D visualization and precise bimanual dexterity, does not outperform laparoscopy, probably because it is still relying on rigid instruments, which results in a reduced workspace while not yet providing haptic feedback to the surgeon. The lack of haptic feedback does not prevent surgery being performed, but when available, haptic feedback enhances the surgeons' situational awareness and thereby increasing safety, improving surgical outcomes, and shortening the learning curve and procedural times. In addition, in RAS the ability to sense contact forces between the instruments and tissues is critical for safe autonomous performance of tasks and procedures.

WO2015/036753 discloses a surgical device and methods using flexible tendons to manipulate a surgical tool within the body of a human or animal subject.

SUMMARY OF THE INVENTION

The present invention provides a medical apparatus comprising: an instrument channel arranged to be inserted into the body of a patient; a medical instrument, or a holder for a medical instrument, arranged to be inserted through the channel into the body of the patient; a support structure arranged to extend around the body of the patient; a plurality of guide ports each arranged to be inserted into the body of the patient; a plurality of control linkages each at least partly supported on the support structure; and a plurality of control actuators; wherein each of the control linkages is arranged to extend through one of the guide ports, to be connected to the surgical instrument, or the holder, and to be moved by a respective one of the control actuators thereby to manipulate the instrument, or the holder, within the body of the patient.

The present invention further provides a medical apparatus comprising: an instrument channel arranged to be inserted into the body of a patient whereby a medical instrument can be inserted through the channel into the body of the patient; a support structure arranged to extend around the body of the patient; a plurality of guide ports each arranged to be inserted into the body of the patient; a plurality of control linkages each at least partly supported on the support structure; and a plurality of control actuators; wherein each of the control linkages is arranged to extend through one of the guide ports, to be connected to the medical instrument, directly or by being connected to a holder for the medical instrument, and to be moved by a respective one of the control actuators thereby to manipulate the medical instrument within the body of the patient.

The patient may be a human or animal patient, and may be referred to as a subject.

At least one of the control linkages may comprise a flexible tendon, which may comprise a cable. At least one of the control linkages may be supported by a pulley, which may be supported on the support structure.

At least one of the control linkages may be a rigid control rod.

The medical instrument may be a surgical instrument or a diagnostic instrument.

The apparatus may further comprise at least one further control linkage at least partially supported on the instrument channel.

The instrument channel may comprise an instrument insertion arm. The arm may be articulated and may comprise a main section and an end section which is connected to the main section by an articulation joint allowing it to articulate relative to the main section.

The apparatus may further comprise an articulation linkage arranged to control the angle of articulation of the end section. The apparatus may further comprise an actuator arranged to actuate the articulation linkage. The at least one further control linkage may be at last partly supported on the end section of the arm. At least one further control linkage may be provided which is at least partly supported on the end section or on the main section. For example where the, or each, further control linkage comprises a tendon, a respective tendon routing end guide may be provided for each control linkage defining the point at which the control linkage extends away from the instrument insertion arm. The tendon routing end guides may be spaced along the instrument insertion arm.

The apparatus may further comprise an endoscope. The endoscope may be slidably mounted on the instrument insertion arm. If the instrument insertion arm is articulated, the endoscope may be slidably mounted on an endoscope track, a part of which may be on the end section of the instrument insertion arm, and part of which may be on the main section of the instrument insertion arm.

The apparatus may further comprise an instrument insertion port through which the instrument channel is arranged to be inserted into the body of the patient. The apparatus may further comprise at least one further control linkage at least partially supported on the instrument insertion port. For example the instrument insertion port may comprise a cable routing end guide from which a cable can extend away from the instrument insertion port.

It will be appreciated that, as well as being used in the abdomen under pneumoperitoneum, the systems can also be used in other anatomical cavities such as the bladder, the eye, or musculoskeletal joints.

The instrument holders, which may be in the form of exchangeable overtubes, allow for attachment of one or multiple instruments, and therefore allow quick exchange of surgical instrumentation. These include compatibility with any commercially available flexible surgical instrument and endoscope.

The guide ports can provide a direct pathway for transferring forces and motion from the external actuators to the surgical instruments within the anatomical cavity. The use of needle-sized ports may enable access without creating or leaving visible scars.

The support structure may comprise a lightweight external scaffold (frame), which may be placed around an anatomical body to fixate the actuators and any additional sensors/instruments. The scaffold may be an external vest in close contact with the patient's anatomy. The spatial arrangement and angulation of the actuators and ports can be modified based on the type of surgery required (e.g. cholecystectomy vs. prostatectomy) and case-specific needs (obese patients, cancer surgery). The size and rigidity of the support structure can be easily controlled by applying vacuum/pressure to a sealed volume of granular/multi-layered material. The support structure can also be the bore of a tomographic imaging device.

The control linkages may comprise multiple cables to manipulate the instrument or instruments within a human or animal body cavity. The instrument may include, or be supported upon, platform to which the cables or tendons are connected. The platform or instrument may manipulated in space by the plurality of cables or tendons, each cable or tending being used to move the platform or instrument in its respective direction. If a platform or instrument holder is used, this enables different surgical and/or diagnostic instruments can be attached or fixed to it.

The ports, or cable channels, may be located in the body's anatomy, at least one cable/tendon may be passed through each channel/port from the inside to the outside for exterior actuation.

The support structure may comprise an exterior structure arranged to be placed onto the body of the human or animal subject.

The exterior structure may be formed to the human or animal body.

The guide ports may be located at locations which are determined so as to provide the workspace for the surgical instruments.

The guide port locations and/or orientations may be determined by pre- and intra-operative images or simulations.

A low-friction material may be used in the guide ports to increase the transmission of forces through the tendons.

The system may further comprise a force sensor arranged to measure the force, which may be a tension force, being transmitted to the instrument by at least one of the control linkages.

The measured force may be used to estimate the forces and torques that the surgical platform and or instruments exert on other bodies. The processor or control unit of the system may be arranged to use this force information or estimation in a number of ways. The estimated instrument forces, which may be end-effector forces applied by the instrument end-effectors, may be used to provide the operator or control system with force information. For example they may be used to provide to the operator with haptic or tactile feedback. The force information may be used for additional safety measures during surgery. The force information may be used to estimate tissue mechanical properties, for example of tissue which is contacted by the instrument. The force information may be used to provide adequate contact forces during autonomous or human-controlled use.

The actuators may include electromechanical components, or fluidic components, or magnetic components, arranged to provide the actuation forces. At least some of the actuation may be performed manually.

There may be at least three control linkages attached to the instrument or platform. Indeed, if the control linkages are flexible tendons, there may be at least six.

The invention further provides a medical apparatus compromising: a plurality of rigid links arranged to manipulate one or more instruments within a body cavity; at least one platform arranged to be manipulated in space by the plurality of rigid links, and to which different surgical and diagnostic instruments can be attached; a plurality of channels arranged to be inserted in the body of a subject through each of which one or more of the rigid links can be guided and attached to the instrument platform, and an instrument channel arranged to be inserted into the body of the subject and through which the instruments can be inserted.

The present invention further provides a medical apparatus compromising: a combination of rigid links and cables to manipulate instruments within a body cavity; at least one platform arranged to be manipulated in space by a combination of at least one rigid link and at least one cable, and to which different surgical and diagnostic instruments can be attached; a plurality of channels arranged to be inserted into the body of a subject through each of which at least one rigid link and/or cable can be guided and attached to the instrument platform.

The present invention further provides a method of configuring a medical apparatus according to the invention, wherein: platform cables are inserted through the body from an inside body cavity to outside and attached to the actuation mechanism; and the at least one platform is inserted into the body cavity via the instrument insertion channel.

The method may include determining the channel positions through the body using pre-operative and intra-operative sources of information. The source of information may include pre-operative and/or intra-operative images.

The invention further provides a medical system compromising a plurality of cameras or optical fibres each arranged to be inserted through a small channel into the body to form a single panopticon, or panoramic endoscopic, image.

Image data from the system may be used to provide an overlay image over an image of the existing anatomy of the subject. The image may be provided to the operator through a virtual environment. The overlay of images can be used to artificially cancel out, i.e. remove from the image, anatomical parts and/or instruments in the body.

The camera positions may be fixed with an exterior structure. The camera position may be determined with exterior tracking mechanisms. The tracking may be performed by an optical tracking system. The tracking may be performed via an electromagnetic tracking system.

The imaging data may be used for screening and diagnostic purposes.

The imaging device may be combined with an energy emitting source, which may be used for therapeutic means. The energy emitting source may be used for generating enhanced information of the body anatomy and/or pathology. The energy emitting source may comprise a light source. Structured light may be used for spatial information. The light may be arranged to emit light is at certain wavelengths. The imaging system may be arranged to collect light at other wavelengths. Additional markers may be used to enhance image information. The energy source may comprise a laser source, which may be arranged to provide laser therapy. The energy source may comprise an ultrasound source for therapeutic ultrasound.

In all aspects of the invention, the exterior support structure may be temporarily attached to the body. Adhesive may be used for temporary attachment. The attachment may be through suction, clamping and/or mechanical enclosure of the anatomy.

The exterior support structure may comprise a medical device, such as the bore, or another part, of a scanner. The exterior support structure may be used to guide the cable or tendon to the actuation mechanism.

The present invention further provides a medical apparatus compromising: a peripheral structure arranged to be placed outside of the human or animal body; at least one platform arranged to be manipulated in space by a plurality of cables, and to which different surgical and diagnostic instruments can be attached; an instrument insertion channel arranged to be inserted into the body of a subject, for receiving at least one instrument; an exterior system comprising at least one actuator for actuating the cables; and a plurality of channels arranged to be inserted in the body of the subject through each of which at least one cable can be guided, from the inside or the outside, for exterior actuation.

Examples of applications open for automation are the implantation of brachytherapy seeds, and automated removal or ablations of tumours under advanced image guidance (fluorescence) or wide-field scanning and classification of tissue areas with ultrasound and/or optical biopsy probes. The systems may also have application in emerging applications like in vivo intra-abdominal/cavity cell therapies and in situ bio-printing of tissues or whole organs, which will require a high degree of precision and autonomy.

The apparatus, system or method may further comprise, in any combination, any one or more features of the embodiments of the invention as will now be described by way of example only with reference to the accompanying drawings.

DESCRIPTION OF THE PREFERRED EMBODIMENTS

Figure 1:
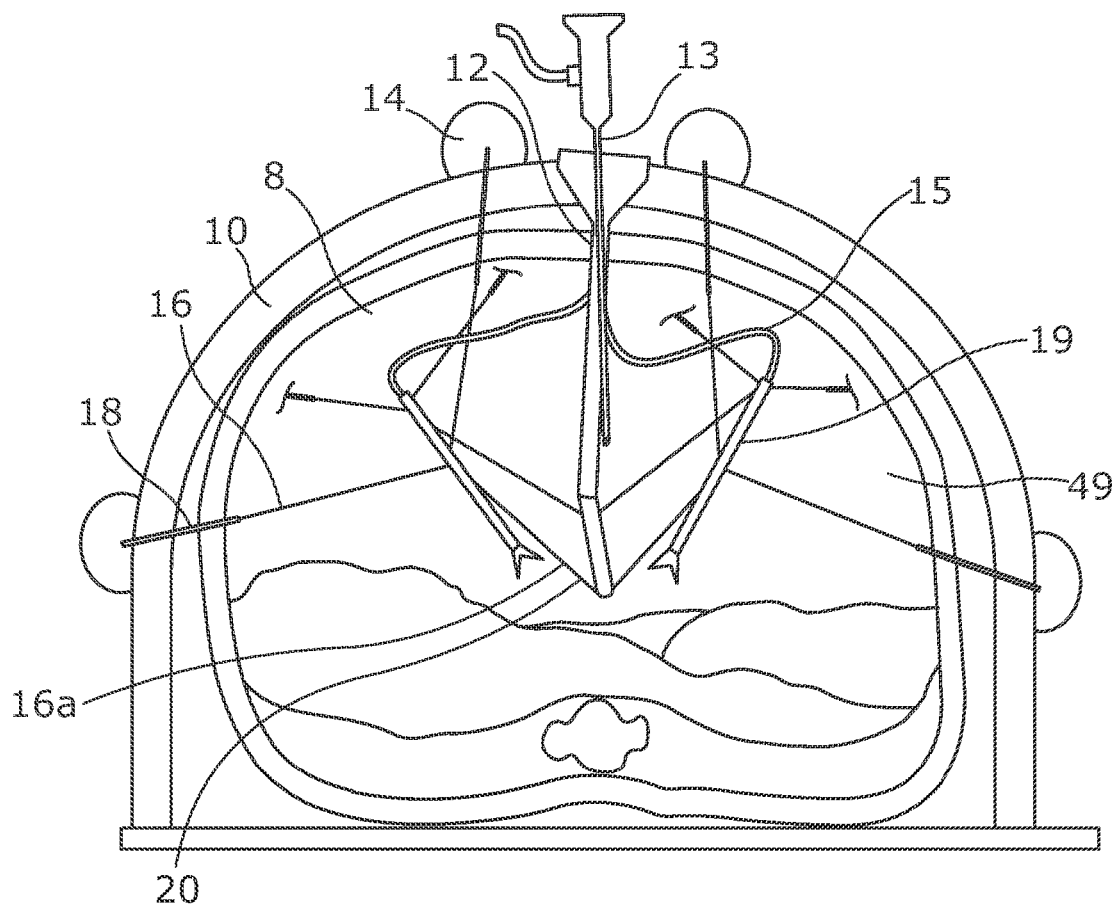
FIG. 1 is a section through a surgical system according to a first embodiment of the invention in use on a patient.

Referring to FIG. 1, a surgical system comprises a support structure 10 arranged to define within it an operating volume within which a part of a subject can be located, so that when the subject is within the operating volume the support structure extends at least part way around, for example over, the body 8 of a patient, an instrument channel 12 through which an endoscope 13 and one or more other surgical or diagnostic instruments 15 can be inserted into the body of the patient, a number of actuator units 14 mounted on the support structure 10, and a number of control linkages 16 connected to the instruments 15 and to the actuator units 14 so that the actuator units can be operated to control movement of the instruments 15 within the body. The control linkages 16 may be flexible tendons, or they may be rigid control rods, as will be described in more detail below. Each of the actuator units 14 comprises a guide port 18 arranged to be inserted into the body of the patient so as to form a port through which one of the control linkages 16 can be moved. If the instruments 15 are rigid, then the control linkages 16 can be connected directly to the instruments. However, the instruments may be flexible, and in any case the system may further comprise an instrument holder 19 arranged to hold the, or each, of the instruments 15 and to which the control linkages 16 are connected. The instrument holder 19 maybe a rigid tube for example.

The number and position of the actuator units 14 need to be sufficient for the instruments 15 to be manipulated with sufficient degrees of freedom to carry out the surgical or diagnostic task. For example there may be a group of three control linkages connected to each end (or to each of two spaced apart positions) on the instrument 15 or instrument holder 19. One 16a of the three control linkages 16 in each group may be a flexible tendon 20 that extends between the instrument channel 12 and the instrument 15. For example, the tendon 20 may extend from the instrument 15 through an aperture in the side or the end of the instrument channel 12, and along the inside of the instrument channel to an actuator (not shown) which may be supported on the support structure 10 or on the instrument channel 12.

Figure 2:
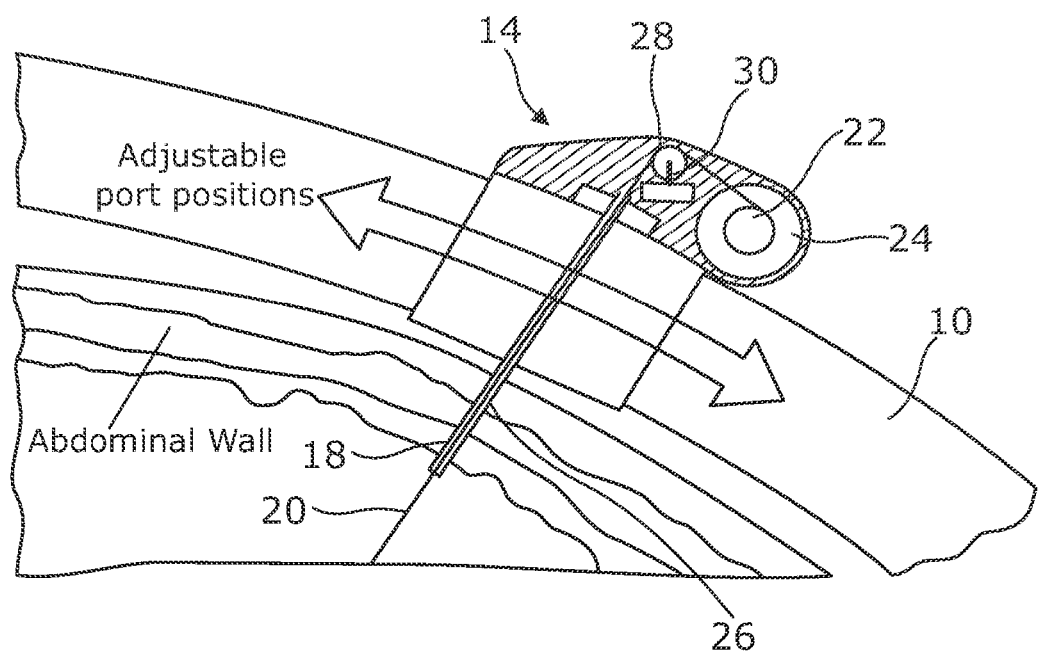
FIG. 2 is a section through an actuator unit forming part of the system of FIG. 1.

Referring to FIG. 2, where the control linkages 16 are flexible tendons 20, each of the actuator units 14 may comprise a spool 22 with the tendon 20 wound on it, and a motor 24 arranged to rotate the spool 22 so as to pull the tendon 20. Each of the actuator units 14 may further comprise one of the guide ports 18 in the form of a thin tube 26 through which the tendon 20 extends. The spool is typically mounted adjacent to the outer end of the guide port tube 26. A pulley 28 may be provided between the spool 22 and the guide port tube 26 with the tendon 20 passing part way around the pulley 28 so as to change the direction of the tendon. A force sensor 30 may then be provided to sense the force applied to the pulley by the tendon 20, and hence to measure the forces being transmitted through the tendon 20 to the instrument 15. This force sensing can be used in a haptic feedback system as will be described in more detail below.

Figure 3:
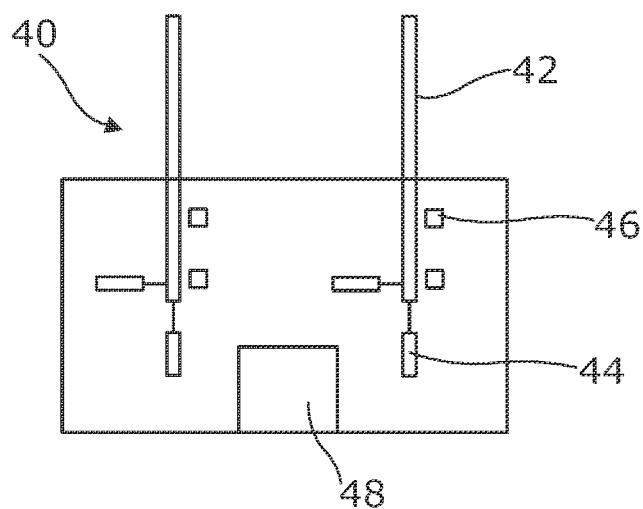
FIG. 3 is a schematic representation of a control unit forming part of the system of FIG. 1.

Referring to FIG. 3, the system further comprises a control unit 40 which provides an interface and allows the surgeon to control the surgical instruments 15 remotely during an operation. The control unit 40 may take any suitable form, and for example may comprise one or more input members 42 which are arranged to be manipulated by the surgeon. The input members 42 may be arranged to simulate the instruments 15. For example in the embodiment shown there are two elongate input members 42 each corresponding to a part of one of the instruments 15. The input members 42 are movably mounted in the control unit 40 so that they can be moved freely in all directions. A number of feedback actuators 44 are also connected to the input members 42 and arranged to apply feedback forces to the input members 42. A number of position sensors 46 are also provided which are arranged to sense the position, and movement, of the input members 42. A processor 48 is arranged to receive signals from the sensors 46 thereby to measure movements of the input members 42, and to control the actuator units 14 to move the instruments 15 in response to those movements. The processor 48 is also connected to, and arranged to receive signals from, the force sensors 30 in the actuator units 16 and is arranged to measure the forces applied to the instruments via the tendons 20, and to control the feedback actuators 44 to apply feedback forces to the input members 42 corresponding to the forces that the instruments 15 apply to the tendons.

Referring back to FIG. 1, the system may be used for laparoscopic surgery or investigation in the abdominopelvic cavity 49, which may be artificially inflated to form a pneumoperitoneum. The instrument channel 12 is inserted through an incision in the abdominal wall and the instruments 15 inserted through the instrument channel 12 with the instrument holders 19 in place over the instruments if they are flexible. If tendons 16a are used which extend up through the instrument channel 12 those are connected to the instruments prior to insertion. Any tendons, or rigid control linkages 16 if they are used, may be inserted either through the guide ports 18 themselves, or though incisions in the patient made prior to insertion of the guide ports 18. If flexible tendons are used they may be inserted on rigid needles which can then be removed once the tendons are attached to the instruments. Alternatively the tendons 16 may be inserted through the instrument channel already attached to the instruments with a loop or other attachment device on their free ends, and then rigid hooked needles inserted through the incisions in the body to pull the ends of the tendons out through the incisions and connect them to the spools 22 of the actuator units. As a further alternative, the tendons 20 may have one end fixed to the instrument 15 or the instrument holder 19, and be inserted into the body with the instrument 15, and then the free end of each tendon pushed out through the abdominal wall or other part of the body, for example using a needle deployed through the instrument channel 12. Once the tendons are connected up, the surgeon can guide the instruments 15 by moving the inputs 42 on the control unit while the processor 48 controls the actuator units 14 to move the instruments and controls the feedback actuators 46 to provide tactile or haptic feedback to the surgeon. The endoscope 13 may be used to aid in the setting up of the system as well as during the surgery or investigation.

It will be appreciated that the instruments controlled using the system described can take a number of forms. For example they may include physiological sensors, a source of radiation and/or radiation detectors, together with the endoscope 13, to facilitate imaging of a part of the body that is not easily accessible for imaging from outside the body. Alternatively, they may include a bio-printing tool which can be used to build up tissue within the body. In a further arrangement each of the instruments may comprise an imaging device or camera. This allows each of the imaging devices to be moved and manipulated independently, or in a coordinated manner. Each of the imaging devices may be arranged to transmit imaging data to the processor 48, which may be arranged to combine the imaging data from all of the imaging devices to form a single imaging dataset, and to control a screen or other display so as to provide enhanced imaging of the subject, such as a panopticon or panoramic image, using the combined dataset.

The processor 48 may further be programmed or otherwise arranged to perform one or more procedures autonomously.

Figure 4:
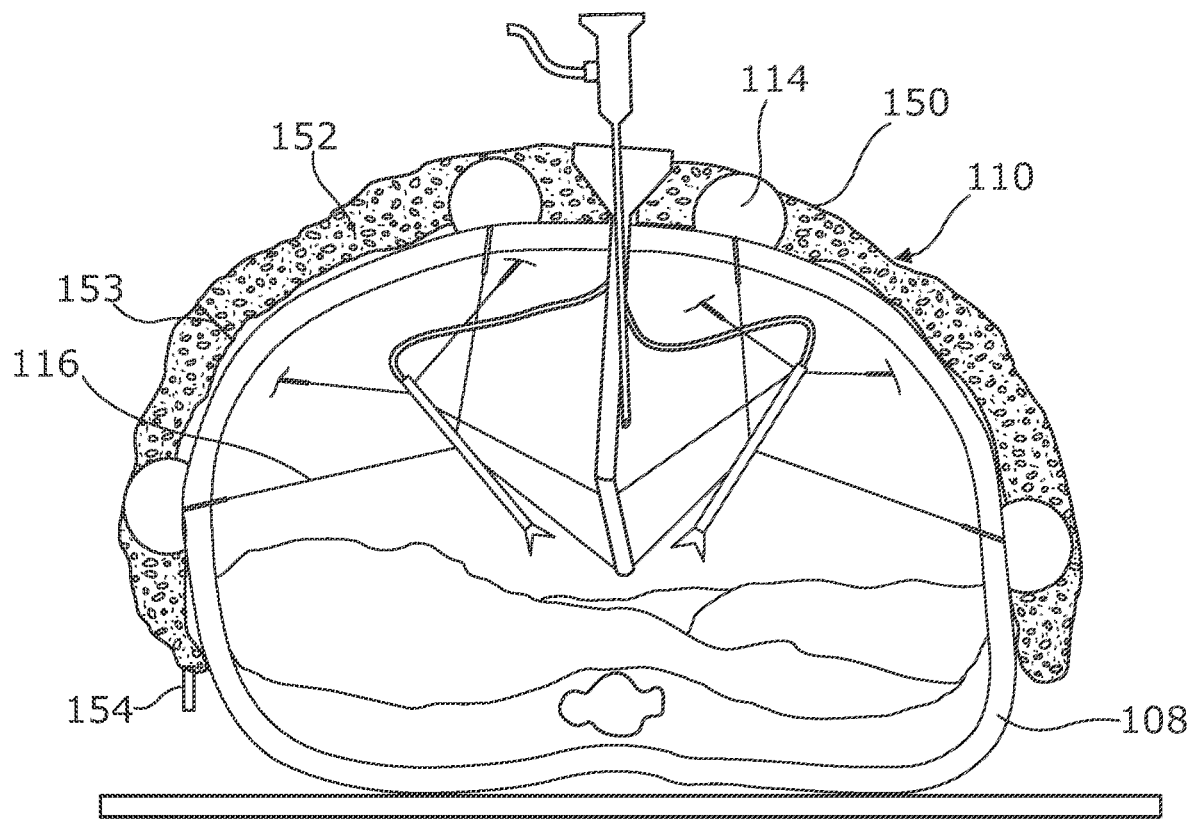
FIG. 4 is section through a surgical system according to a second embodiment of the invention.

The support frame 10 of FIG. 1 may take a number of forms, such as moulded plastics or a metal frame structure. However it is typically rigid and therefore not easily usable with patients of very different sizes, since it is preferable for the guide ports 18 to be mounted close to the body 8 of the patient. Referring to FIG. 4, in which features corresponding to those in FIG. 1 are indicated by the same reference numeral increased by 100, in a second embodiment the support structure 110 is a granular jamming structure arranged to be fitted around the patient 108 when in a flexible state and then solidified so as to form a rigid support structure close to the patient's body. The support structure therefore comprises a flexible airtight container or bag 150 containing granular material 152. The bag 150 may initially be arranged to be flat and rectangular so that it contains a flat layer of the granular material 152, which can be wrapped around the patient as shown in FIG. 4. If the bag is of suitable flexible material such as latex it may be initially of various shapes. The bag 150 may be partitioned by porous dividers 153 so as to prevent too much movement of the granular material 152 whilst allowing air to be evacuated from the whole of the bag via a suitable port 154. The actuator units 114 are fixed within the bag 150 and at least partly surrounded by the granular material 152 so that when the air pressure in the bag 150 is reduced the resulting rigid support structure supports the actuator units 114 in respective fixed positions. Once the rigid support structure is in place around the patient, the system operates in the same way as that of FIG. 1. In a modification to this arrangement, laminar jamming material, which is laminar or a combination of laminar and granular material, may be used in the support structure, instead of the granular material 152, which can be made rigid with the application of positive or negative pressure.

Figure 5:
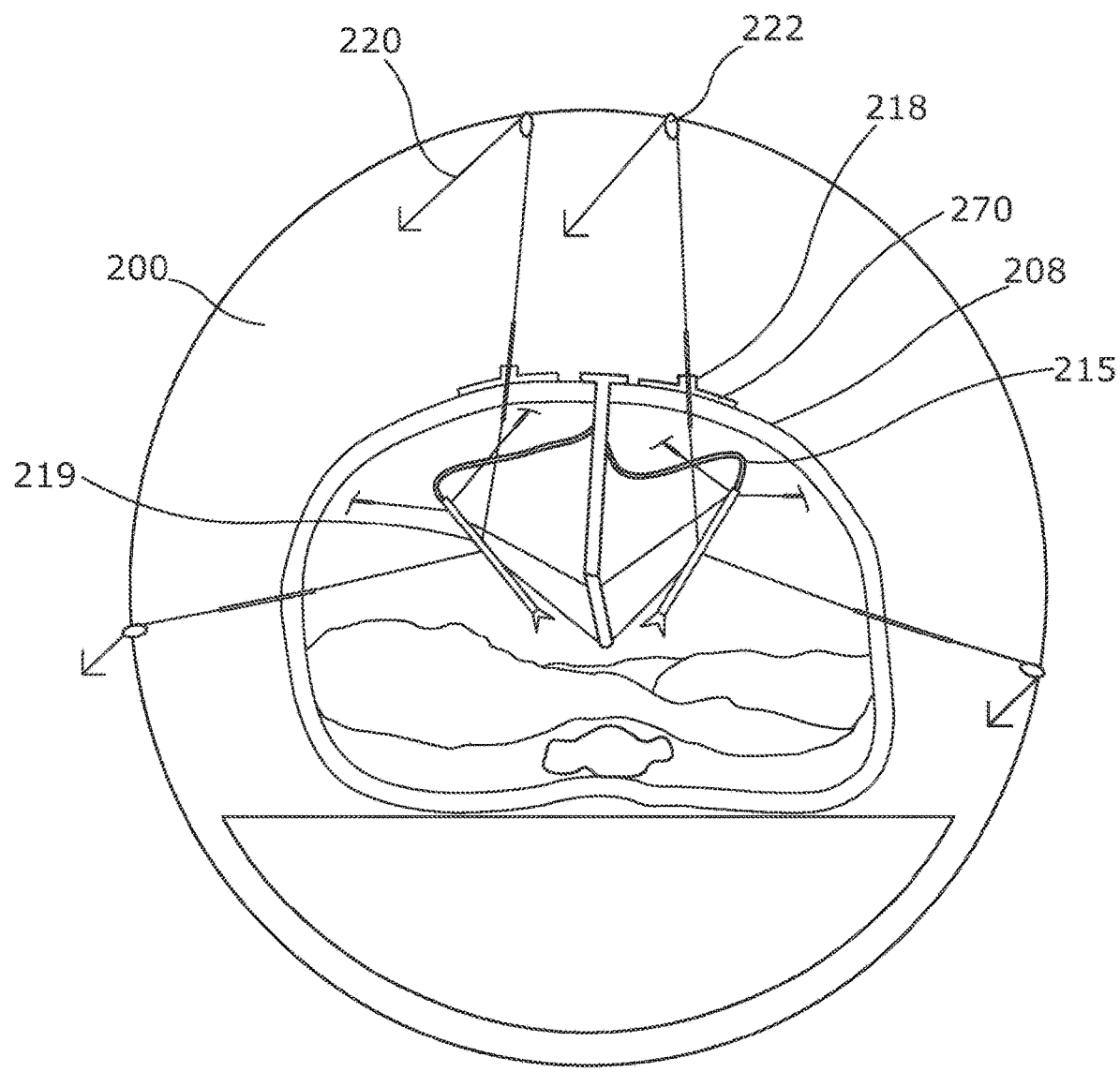
FIG. 5 is a section through a surgical system according to a third embodiment of the invention.

Referring to FIG. 5, in a further embodiment of the invention the system is designed for operation within the bore 200 of a tomographic imaging device, such as an MRI scanner. Again features corresponding to those in FIG. 1 are indicated by the same reference numerals increased by 200. In this case each of the guide ports 218 is supported in a respective adhesive patch 270 arranged to be placed on the skin of the patient 208 so that they can be inserted into the patient 208 and then held in place by the adhesive patch 270.

Rather than adhesive, the patches may be secured to the body in other ways, such as stitching or suction cups. The motors which apply forces to the tendons 220 are located remotely and not shown in FIG. 5, but the pulleys 222 are each mounted on the MRI scanner around the bore 200. Therefore each of the tendons 220 extends from the instrument 215 out of the patient through its respective guide port 218 and then on outwards to the pulley 222. From the pulley 222 each of the tendons extends along the inside of the scanner bore 200 to the spool and motor unit which are located remotely for example at one end of the scanner bore 200. All of the components of the system which are to be located within the MRI scanner bore can be made of plastics or other non-magnetic materials so that they are fully MRI compatible.

In a modification to the embodiment of FIG. 5, rather than using an MRI scanner to support the control linkages, each of the adhesive patches 270 may be provided with an individual support structure which supports an actuation unit, which may correspond to those of FIG. 1. Therefore the support structures which support the actuator units are attached directly to, and supported on, the body of the subject. This has the advantage that the surrounding support structure does not need to be erected around the subject. However it has the disadvantage that the support structures are not rigidly fixed in space, but may move, for example if the subject breathes. In order to compensate for this, the movement may be sensed by a movement sensor which is arranged to send signals to the processor, which in turn is arranged to control the actuator units to move the control linkages, relative to the actuator units, so as to compensate in real time for the movement of the support structures on the body. The movement sensor may be the laparoscope (not shown in FIG. 5 but corresponding to that 13 of FIG. 1). Alternatively it may comprise an internal or external optical or electromagnetic tracking or imaging system, or one or more imaging devices mounted on, or forming, the medical instruments.

Referring back to FIG. 2, in the system of FIG. 1 as the instruments 15 move within the patient, the guide ports 18 may be arranged to rotate so as to remain aligned with the direction in which the tendons 20 extend from the inner end of the guide ports 18 to the instruments 15. This may be preferable if flexible tendons 20 are used as the control linkages, although in this case if relatively short guide ports 18 are used it may not be essential. However such rotation or pivoting of the guide ports 18 is essential if rigid guide rods are used. If the guide ports 18 are arranged to pivot in the actuator units, in order to minimize damage to the patient's body 8, it is desirable for each of the guide ports 18 to be supported on a remote centre of motion mechanism so that, while they are supported within the actuator units 14, they are rotated about a centre of motion which is located just within the body 8. For example if the system is to be used in the abdomen, the centre of motion of the guide ports 18 may be located in the abdominal wall. That means that the guide ports 18 will each pivot about that centre of motion as the instruments 15 move within the abdomen.

Figure 6:
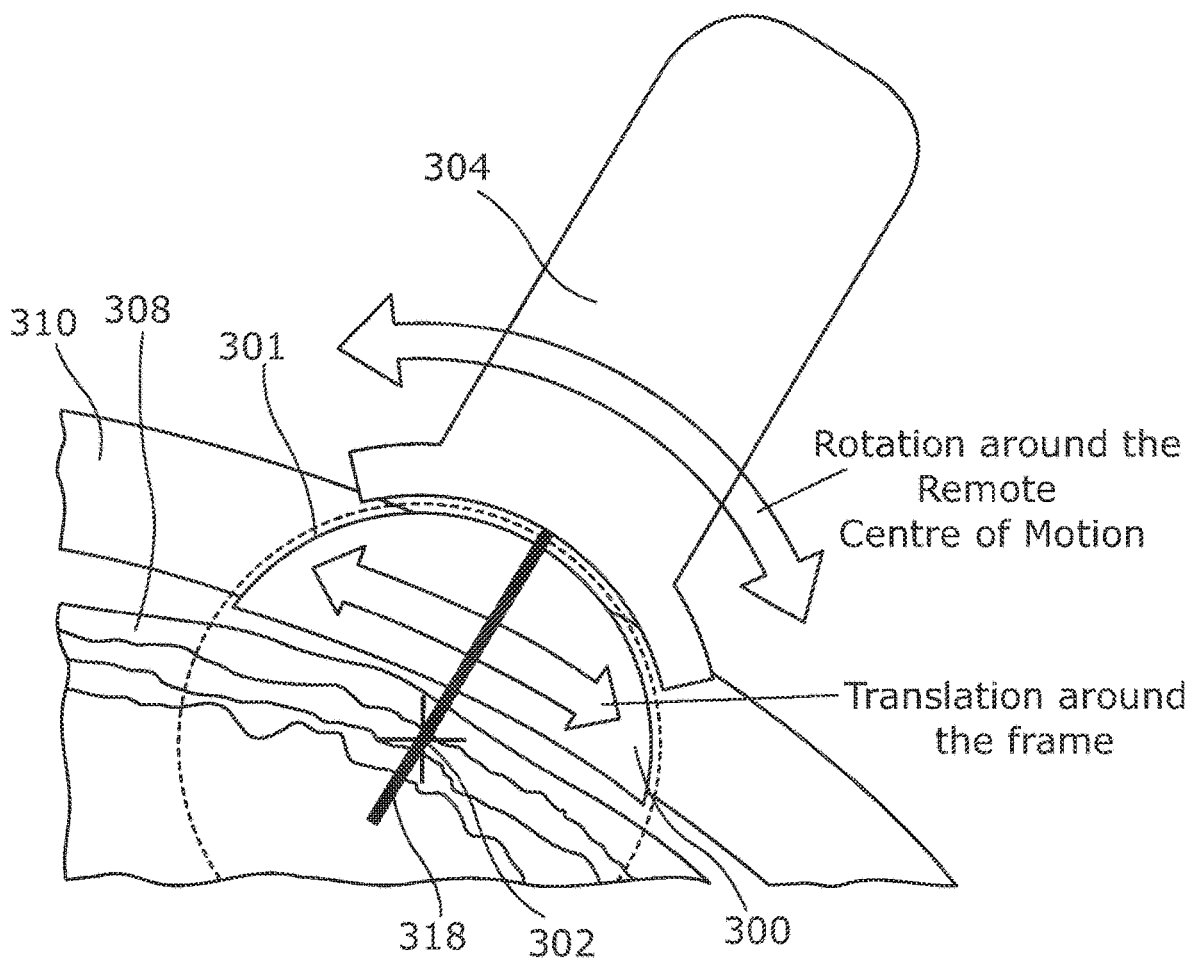
FIG. 6 is a section through an actuation unit forming part of the systems of FIGS. 1 and 4.

Referring to FIG. 6, the actuator units 14 may for example each comprise a guide mounting 300 mounted in the support structure 10 which has a part-spherical outer surface 301 which is curved about a centre of curvature 302. The guide mounting 300 is hollow and has a large aperture though it so that the control linkage 16 can extend through it. An actuator housing 304, which houses the actuator, may be mounted on the curved outer side of the guide mounting 300 so as to slide over the mounting 300, moving about the centre of curvature 302 which forms the centre of motion of the mechanism. The centre of motion 302 is located at a point spaced from the support structure, which can be within the abdominal wall when in use. The control linkage 16 may extend from the actuator housing 304 through the guide mounting 300. In operation as the instruments 15 are moved within the abdominal cavity, the actuator housing 304 rotates about the centre of motion 302. This arrangement can be used with flexible tendons or rigid control rods as the control linkages.

The mounting 300 may be fixed in the support structure 310, or it may be movably mounted in the support structure 310, for example on tracks or guides, so that it can be translated around the support structure. This allows the location of the ports 318 to be adjusted relative to the support structure 310 and hence also relative to the subject 308.

Figure 7:
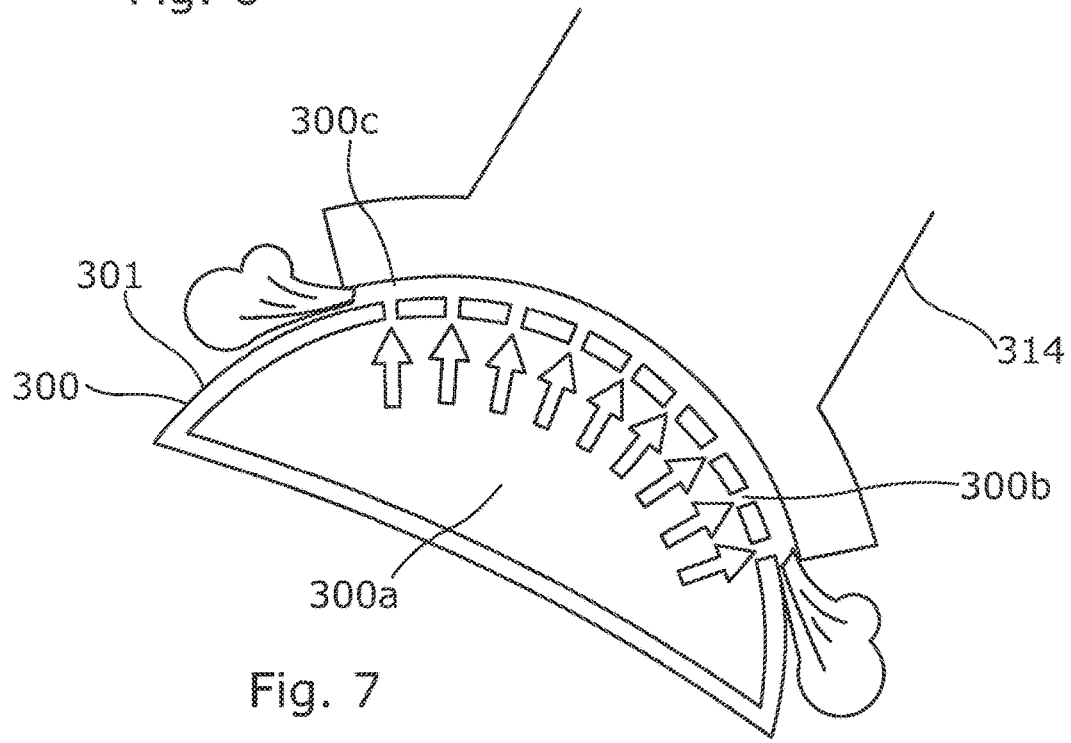
FIG. 7 is section through part of the actuation unit which is a modification of the actuation unit of FIG. 6.

Referring to FIG. 7, the mounting 300 may have one or more pressure chambers 300a formed therein, with apertures 300b defined in its outer surface 301 to allow air to escape from the pressure chambers 300a to the gap 300c between the actuator housing 314 and the mounting 300. This allows pressurised air to be pumped into the pressure chambers 300a which will escape through the apertures 300b into the gap 300c thereby providing a low-friction interface between the actuator housing 314 and the mounting 300.

Figure 8:
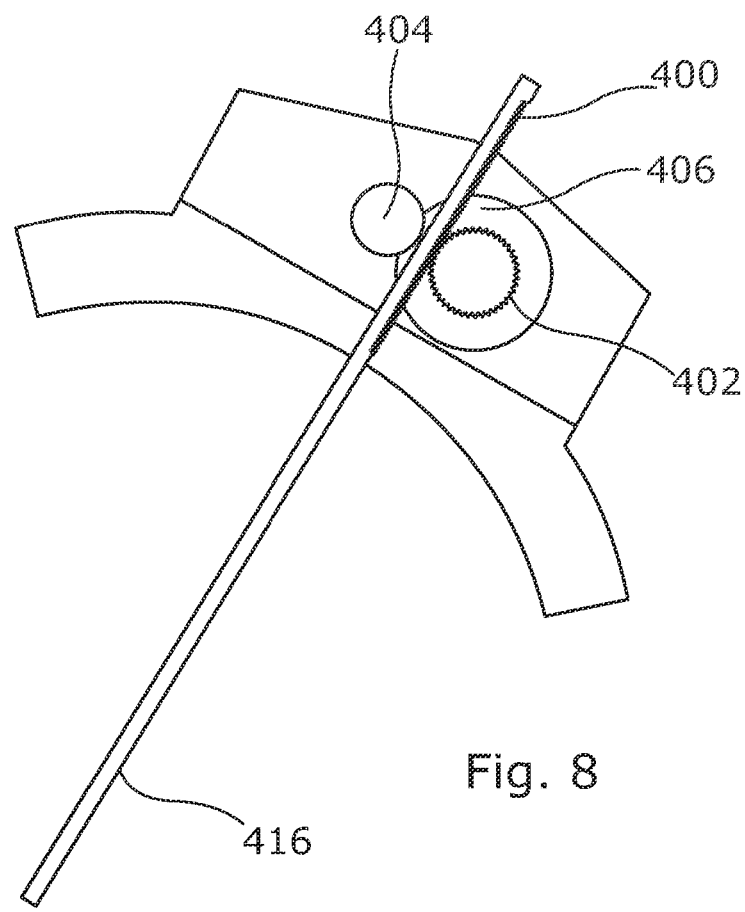
FIG. 8 is a schematic representation of a rack and pinion drive forming part of the actuation unit of FIG. 6.

Referring to FIG. 8, each of the actuator units may comprise, within the actuator housing 304, a rack and pinion type actutator, with a toothed rack 400 connected to the control linkage 16, and a toothed pinion wheel 402 and a guide wheel 404 arranged to grip the rack and move it in an out of the patient's body under the power of a motor 406. This type of actuator can be used with either a rigid or a flexible control linkage 416. While no force sensing is shown in FIG. 8, this can be provided by means of a load cell connecting the control linkage 16 to the rack 400, or by sensing the torque of the motor 406, for example.

Figure 9:
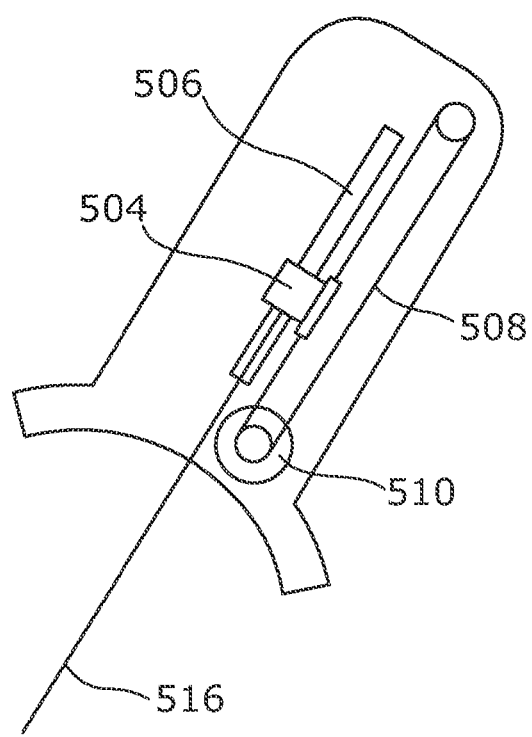
FIG. 9 is a schematic representation of a belt drive which is an alternative to the drive of FIG. 8.

Referring to FIG. 9, as an alternative drive mechanism, each of the actuator units may comprise, within the actuator housing 304, a belt drive in which the end of the control linkage 16 is connected to a linear guide 504 which runs along a linear rail 506 and incorporates a load cell for sensing the forces in the control linkage 16. The linear guide 504 is connected to a drive belt 508 which is driven by a motor 510. The motor 510 can therefore be operated to move the linear guide 504 along the rail 506 thereby to move the control linkage 16.

Figure 10:
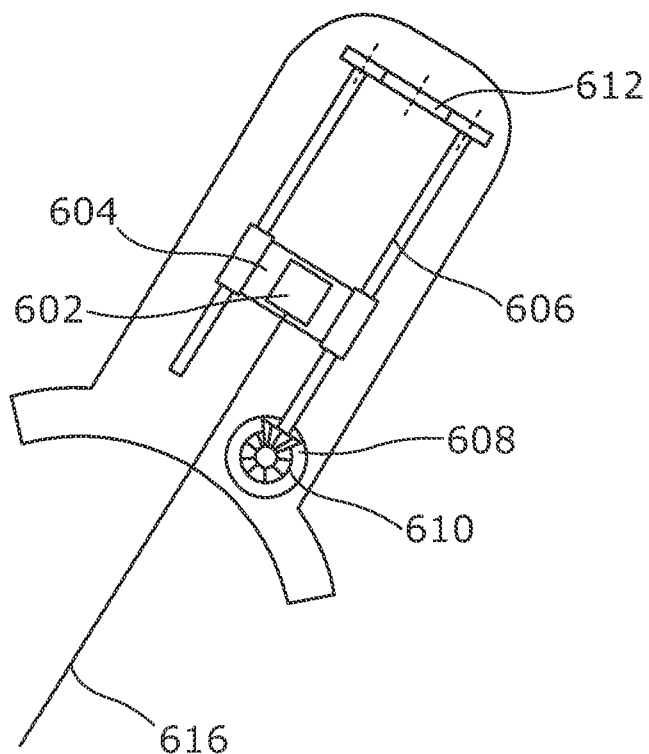
FIG. 10 shows a screw drive which is an alternative to the drive of FIG. 8.

Referring to FIG. 10, as an alternative drive mechanism, each of the actuator units may comprise, within the actuator housing 304, a screw drive mechanism, in which the end of the control linkage 16 is connected, via a load cell 602 to a linear guide 604 which is mounted on two threaded drive rods 606 so that rotation of the drive rods 606 moves the control linkage 616 along them. A first one of the drive rods 606 is driven from a motor 608 via a crown and pinion drive 610, and the second of the drive rods 606 is driven from the first by a set of gears 612. In a modification to this arrangement only one of the drive rods 606 is used and the gears 612 therefore omitted.

Figure 11:
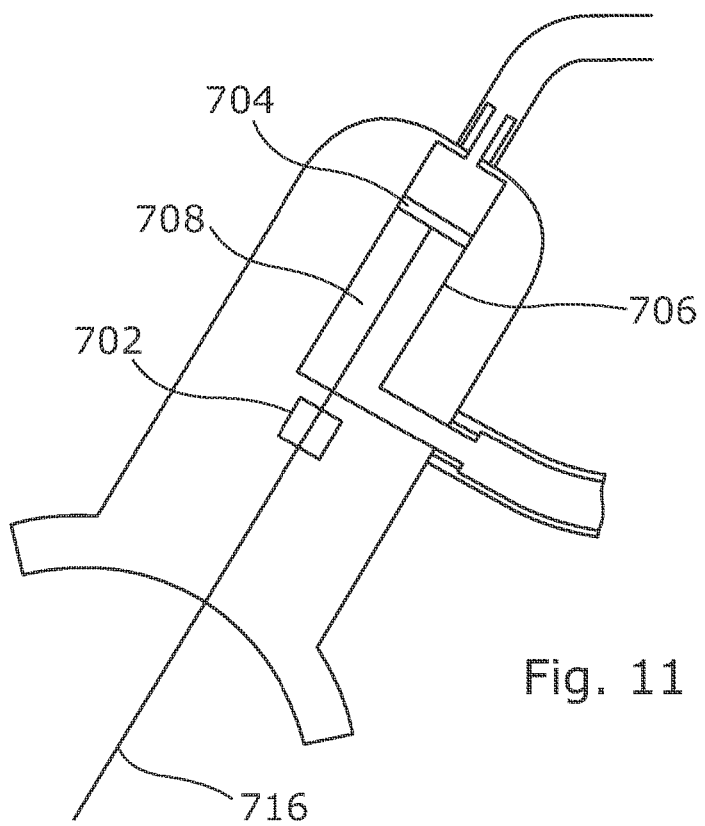
FIG. 11 shows hydraulic or pneumatic drive which is an alternative to the drive of FIG. 8.

Referring to FIG. 11, as an alternative drive mechanism, each of the actuator units may comprise, within the actuator housing 304, a fluid drive mechanism, in which the end of the control linkage 16 is connected via a load cell 702 to a piston 704 which is movable in a cylinder 706 in response to the supply of pressurised fluid to the pressure chambers 708 on either side of the piston 704. The fluid may be hydraulic fluid, or air or other gas if the actuator is pneumatically operated.

Figure 12:
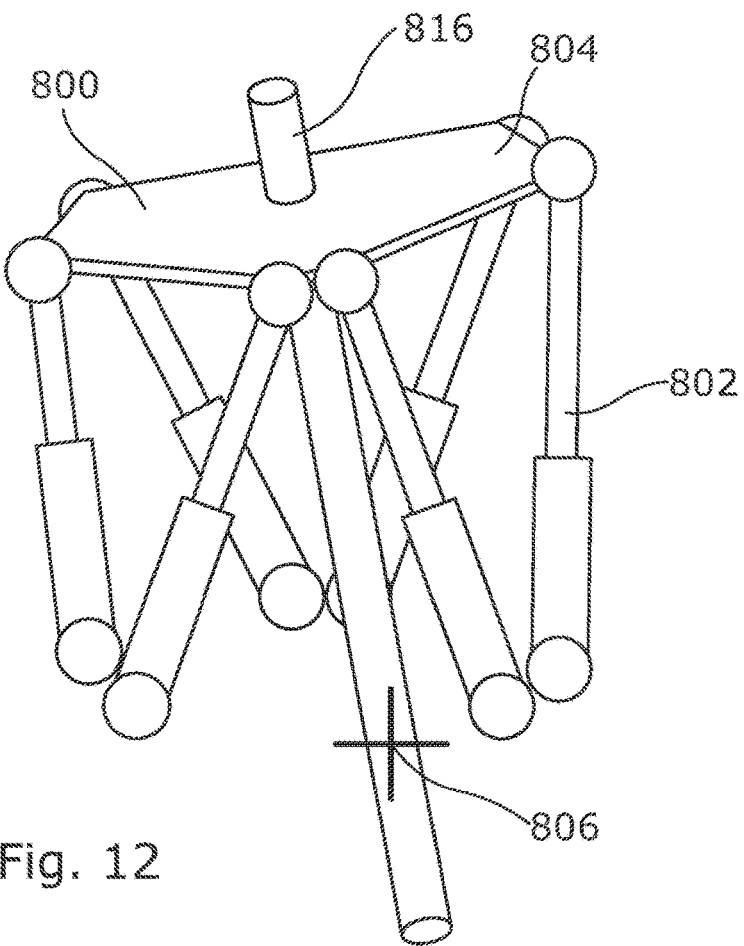
FIG. 12 shows a Gough-Stewart drive forming part of an actuation unit of a system according to a further embodiment of the invention.

Referring to FIG. 12, as an alternative arrangement, each of the actuator units may comprise a drive platform 800 connected to the support structure 10 by means of a number of linear actuators 802, for example six linear actuators 802 as shown. Each of the linear actuators 802 has one end rotatably connected to the support structure and the other end rotatably connected to the drive platform 800. The linear actuators are arranged in a non-parallel configuration so that they can apply forces in different directions. It will be appreciated that the arrangement allows the drive platform 800 to be moved in any direction, and rotated in any direction, giving six degrees of freedom. The rigid control linkage 16 (or the rigid tubular guide port if a flexible control linkage is used) is rigidly connected to the drive platform 800 so that, in use, it extends into the body of the patient. The linear actuators 802 can be controlled so as to rotate the drive platform, and hence also the drive member 16 (or the tubular guide port), about a centre of motion 806, as well as to move the drive member so that it moves along its length through the centre of motion 806. It will be appreciated that a sensor for sensing the load in the control linkage 16 could be provided in the form of a load cell between the control linkage 16 and the drive platform 800, or by sensing the force in each of the actuators 802.

Figure 13:
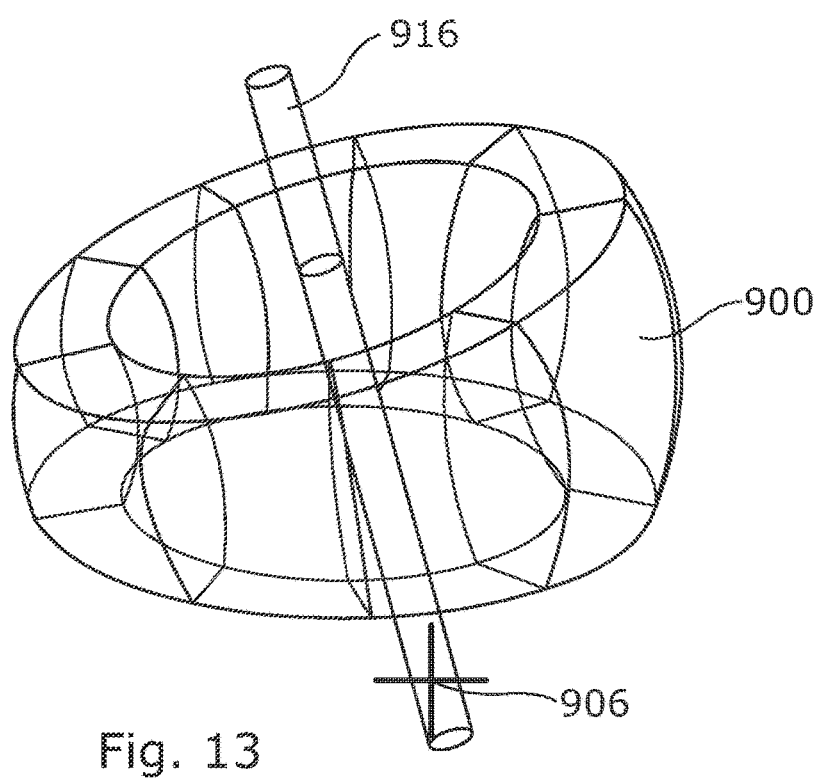
FIG. 13 shows a soft hydraulic or pneumatic drive forming part of an actuation unit of a system according to a further embodiment of the invention.

Referring to FIG. 13, as a further alternative arrangement each of the actuator units comprises a drive platform similar to that of FIG. 12, but the drive platform is connected to the support structure by a number of inflatable chambers 900 which are arranged around the axis of the guide port or control linkage 16. Each of the inflatable chambers has an inlet/outlet port which is connected to a pressure source and can be inflated or deflated as required. Coordinated inflation and deflation of different chambers 900 can be used to control movement of the drive platform, and hence also the guide port or control linkage 16, with movement being about a remote centre of motion 906, which can again be located in the patient, for example in the abdominal wall.

Figure 14:
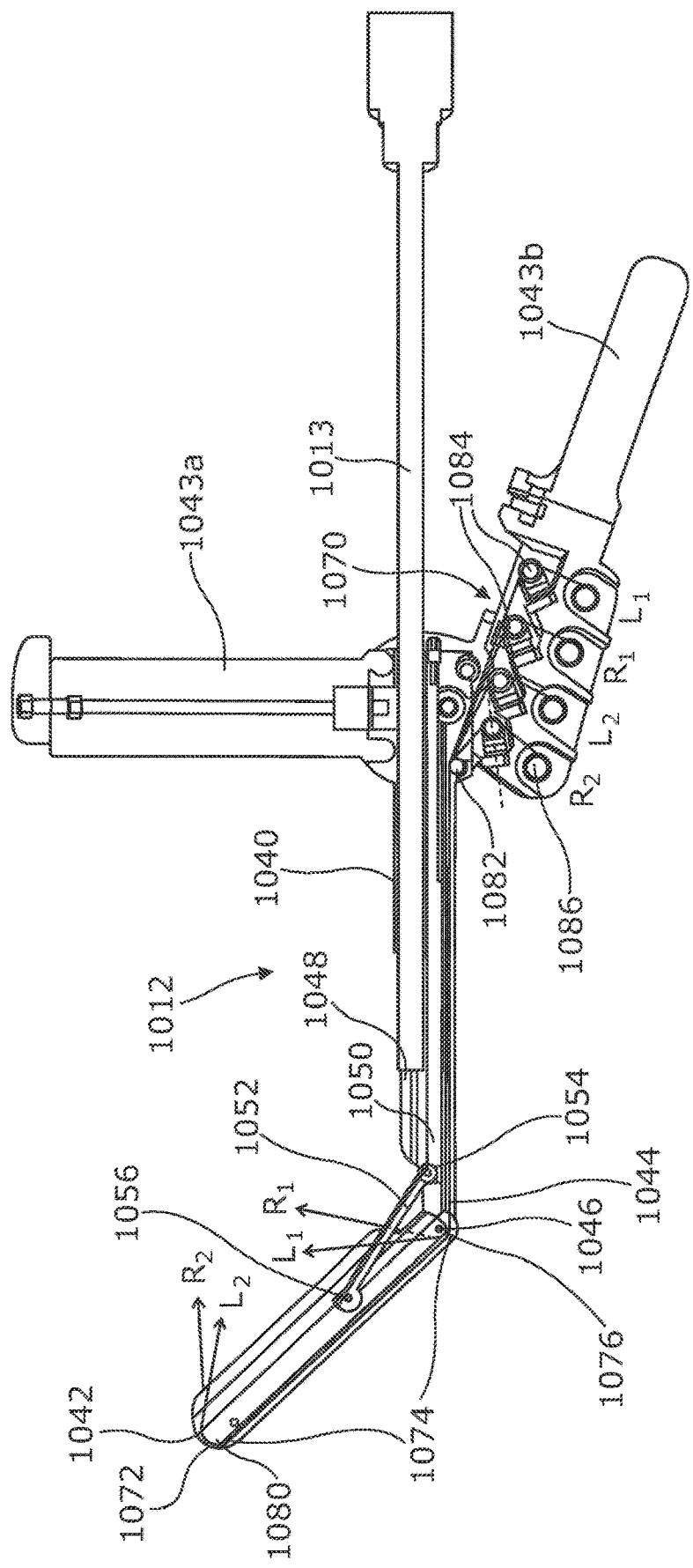
FIG. 14 is a section through a transperitoneal arm forming part of a system according to a further embodiment of the invention.

Referring to FIG. 14, the instrument channel may comprise an articulated arm 1012, which may be referred to as a transperitoneal arm. The arm 1012 may comprise a main section 1040 and an end section 1042, with a top handle 1043a and a back handle 1043b connected to the main section 1040 to allow it to be manipulated. The end section 1042 may be pivotably connected to the distal end 1044 of the main section 1040 by a pivot pin 1046 or other suitable hinge mechanism. The endoscope 1013 may be slidably mounted on the main section 1040, for example with an endoscope track 1048 formed in the main section 1040 along which the endoscope 1013 is arranged to slide. Part of the endoscope track 1048 may also be formed in the end section 1042 so that when the end section 1042 is pivoted so as to be aligned with and parallel to the main section 1040 the endoscope 1013 can be slid along substantially the full length of the articulated arm 1012. Articulation of the arm 1012 may be controlled by an articulation linkage, which may comprise a push rod 1050 and articulation link 1052. The push rod 1050 may be slideable along the length of the main section 1040 and the articulation link 1052 may be pivotably connected to the push rod 1050, for example at its distal end 1054, and to the end section 1042 at a point 1056 spaced from the pivot axis of the hinge mechanism 1046.

Figure 15:
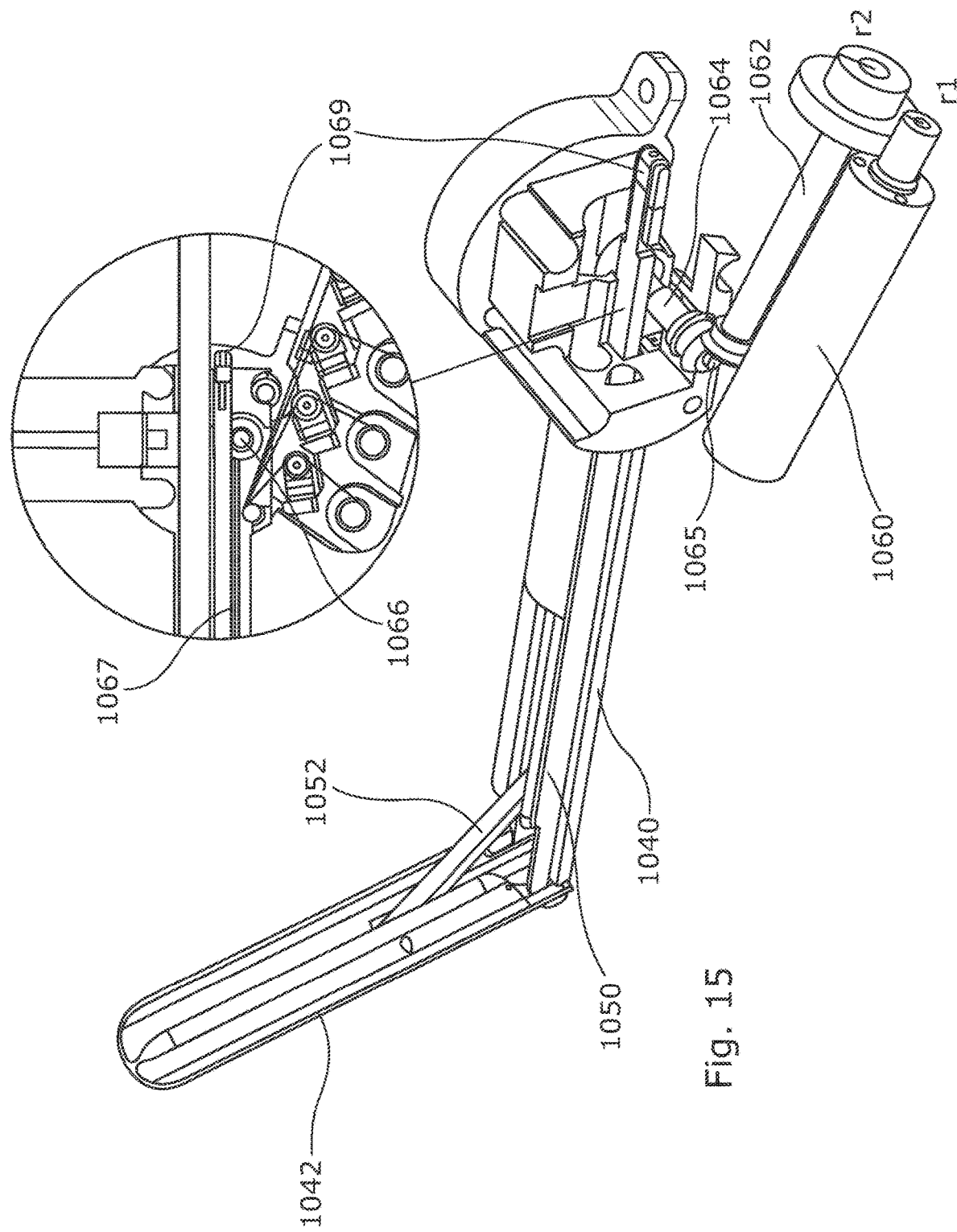
FIG. 15 is a perspective view of the articulation mechanism of the transperitoneal arm of FIG. 14.

Referring to FIG. 15 the articulation linkage 1050, 1052 may be driven by an actuation motor 1060 for example via a gear shaft 1062, and a drive shaft 1064 connected to the gear shaft by mitre gears 1065 connected to a cable drive wheel 1066 which may drive a cable 1067 which is in turn connected to the push rod 1050. A cable tensioner 1069 is provided to tension the cable 1067 so as to ensure accurate control of the pushrod 1050. The actuation motor 1060 can therefore be operated to drive the push rod 1050 along the main section 1040 of the arm 1012 thereby to move the end section 1042 of the arm through a range of articulation angles between an aligned position in which it is parallel to and aligned with the main section 1040 and an angled position, such as that shown in FIGS. 14 and 15, in which it is at an angle to the main section 1040.

Referring back to FIG. 14, at least one, and typically several, of the tendons or cables for controlling the medical instrument may extend along the transperitoneal arm 1012, in a similar manner to the arrangement of FIG. 1, In the embodiment of FIG. 14 there are four cables $L_1$, $L_2$, $R_1$, $R_2$ extending along the arm 1012. For each of the cables a cable routing 1070 is provided on the arm which defines the route of the cable along the arm, ending with a routing end guide 1072. The routing end guide 1072 forms the end of the cable routing and defines the point at which the cable extends away from the arm 1012 towards the medical instrument. A single component, which may be a moulded PTFE guide component 1074, may form the routing end guide for all of the cables $L_1$, $L_2$, $R_1$, $R_2$. For example the PTFE guide component 1074 may extend along the end section 1042 of the arm, and may incorporate a guide surface 1076 near its proximal end for one or more of the cables $L_1$, $R_1$ which are routed to the proximal end of the end section 1042 of the arm 1012, and a guide surface 1080 for one or more of the cables $L_2$ $R_2$ which are routed to the distal end of the end section 1042. The rest of the routing 1070 may comprise one or more pulleys 1082 around which the cables pass, ending with a load cell pulley 1084 and a cable spool 1086 for each of the cables $L_1$, $L_2$, $R_1$, $R_2$. Each of the cable spools 1086 may have a drive motor 1088 arranged to drive the spool to pull its respective cable or to release it to allow the cable to be pulled from the spool 1086. The drive motors 1088 of the spools 1086 may be controlled by a controller as described above with reference to FIG. 1 to control the position of a medical instrument.

Figure 16:
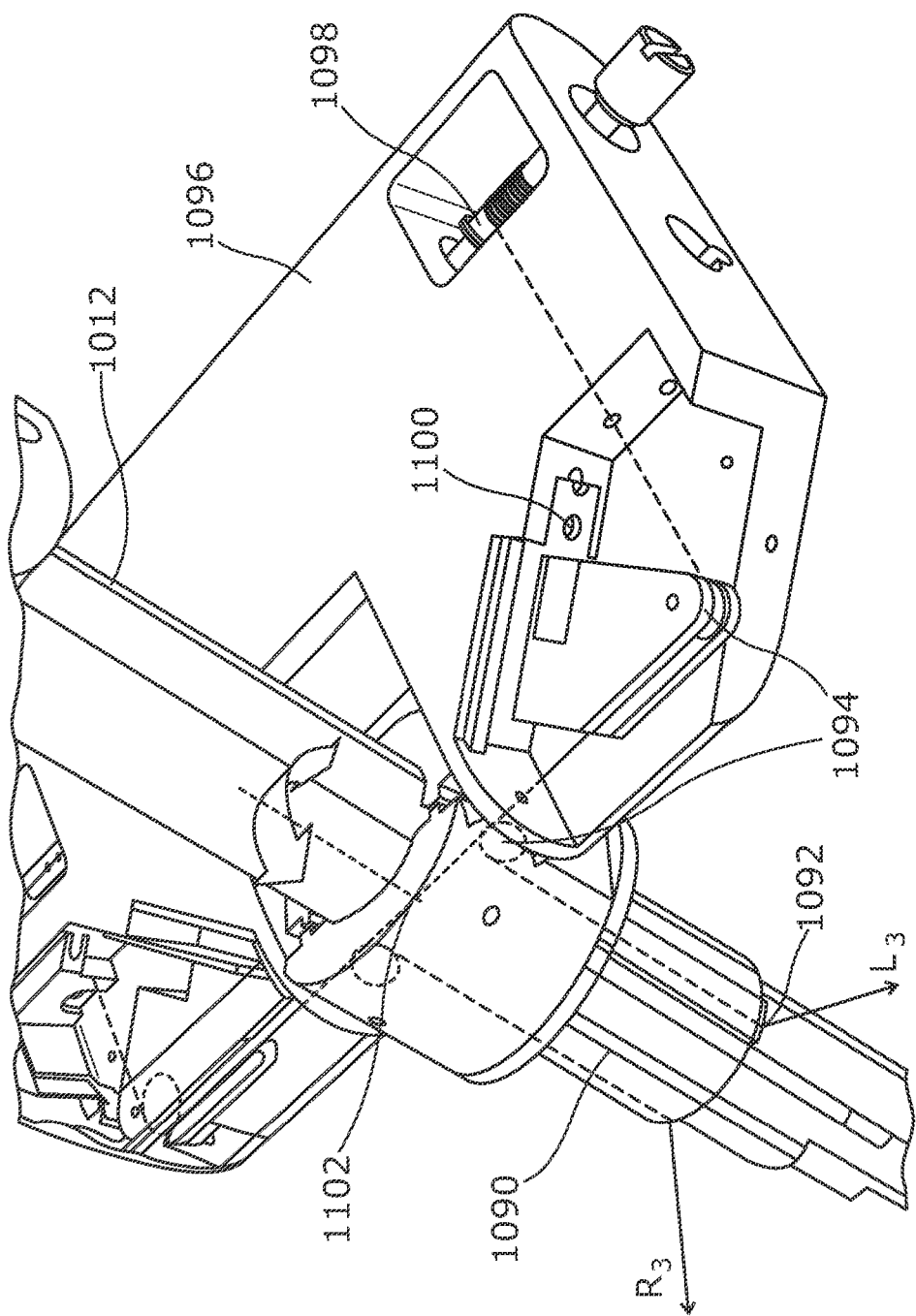
FIG. 16 is a perspective view of part of the transperitoneal arm of FIG. 14.

Referring to FIG. 16, the transperitoneal arm 1012 may be arranged to slide through an umbilical port 1090 which may be mounted on the support structure, and arranged to extend into the body of the patient, so that the transperitoneal arm 1012 can be moved into and out of the body of the patient. The umbilical port 1090 may also form routing for one or more further cables $R_3$, $L_3$ and may form routing end guides, for example in the form of eyelets 1092, for those further cables $R_3$, $L_3$. The routing for these further cables $R_3$, $L_3$ may further comprise one or more pulleys 1094 mounted on the umbilical port 1090. A cable control platform 1096 may be connected to the umbilical port 1090 to support cable spools 1098 and loadcell pulleys 1100 for each of the further cables $R_3$, $L_3$. The cable control platform may be pivotably connected to the umbilical port 1090 with a pivot axis 1102 aligned with the pulleys 1094 on the umbilical port 1090 so that the umbilical port 1090 and the cable control platform can rotate relative to each other without affecting the operation of the cables $R_3$, $L_3$.

In operation the transperitoneal arm 1012 may be inserted into the patient's body in a straight configuration, with the endoscope 1013 advanced to the distal end of the end section 1042 of the arm. When the arm is inserted, the endoscope 1013 may be partially withdrawn to the position shown in FIG. 14, and then the end section 1042 may be articulate to the required angle. The relative positions of the routing end guides for each of the cables $L_1$ $L_2$ $L_3$ $R_1$ $R_2$ $R_3$ can be varied as required by moving the transperitoneal arm 1012 through the umbilical port 1090 and by adjusting the angle of articulation of the arm 1012. The cables $L_1$ $L_2$ $L_3$ $R_1$ $R_2$ $R_3$ can be attached to the medical instrument before it is inserted, and further cables extending through ports supported on a support structure as described above with reference to FIGS. 1 to 13 may be connected to the instrument so as to provide full control of the instrument in all six degrees of freedom.

It will be appreciated that having the routing end guides for the control cables at different positions spaced along the transperitoneal arm 1012, in particular in combination with the articulation of the transperitoneal arm 1012, allows for a large number of options for the configuration of the control cables, and that the structure of the transperitoneal arm 1012 and the number and location of the cable routing end guides can be varied in many ways depending on the nature of the medical instrument and the procedure to be performed.

Embodiments of the invention may have a number of advantages, such as:

- High instrument dexterity and force exertion capability. When compared to existing robotic-assisted surgery (RAS) systems, the parallel actuation method of some embodiments of the invention surpasses them with proven dexterity and high force exertion capability. They also allow intuitive and direct control of the instrument (6 degrees of freedom), real-time imitation of surgeons' motions without complex compensations (no fulcrum). Their high force exertion capabilities may bring back open-surgery's whole organ holding/retraction, something only partially possible in laparoscopic surgery, and impossible for current snake-like surgical robots.
- High accuracy and high-force sensitivity. The micro-ports enable a direct link between the system actuators and instruments, thereby reducing friction and increasing positional and force sensing accuracy.
- Haptic feedback. The high force-sensitivity allows for haptic feedback to the surgeon, enhancing the surgeon's situational awareness, shortening the learning curve and procedural times. Most of current commercially available RAS systems lack haptic feedback, only provide it with a low resolution.
- Safe autonomous motions. High accuracy and high force-sensitivity can enable the integration of safe autonomous motions. Safe autonomous motions are essential when performing procedures which are impossible or rather cumbersome to perform by the human operator. Examples of applications open for automation are the implantation of brachytherapy seeds, and automated removal or ablations of tumours under advanced image guidance (fluorescence) or wide-field scanning and classification of tissue areas with ultrasound and optical biopsy probes. The systems may also have application in emerging applications like in vivo intra-abdominal/cavity cell therapies and in situ bio-printing of tissues or whole organs, which will require a high degree of precision and autonomy.
- Ultra-minimally invasive (scar-less) surgery. The use of needle-sized micro-ports can reduce the invasiveness, and thus, trauma to the patient and prevent the formation of visible scars. The endoscope and flexible instruments may be inserted through one small incision. Scar formation can be hidden by using a natural anatomical orifice or the umbilicus (navel).
- Fast conversion to open surgery. An exterior support structure allows quick deployment and removal, which are essential for reduced setup time, operating time, and emergency conversion to open surgery, if necessary.
- Reduced footprint for mobile military/emergency surgery. Remote surgery can be performed on soldiers wounded in the battlefield. The support structure can be integrated into advanced battlefield extraction stretchers. Quick exploratory laparotomy and abdominal vessels clamping can be performed by a remote surgeon, while the wounded soldier is being extracted (inside ground or air ambulances).
- Workspace customizability to accommodate wide range of surgical applications. The exterior support structure may be reconfigurable to enable port-placement modularity. This may be advantageous as the system may be modified to any of various procedures in chest, abdomen, pelvic surgery, or any cavity, natural or virtual, of any size (e.g. eye, knee arthroscopy), and can be modified to deal with patient-specific requirements. Also, it can become a tomographic imaging device by integrating into the structure of imaging detectors (e.g. ultrasound, near infrared spectroscopy), therefore allowing image-guided surgery.
- MRI compatibility/integration with MRI to form a surgical pod. The support structure may, as described above, be the bore of (any) MRI scanner or other tomographic imaging device. Current surgical robotic systems use several solid and metal links to transmit actuation forces to its surgical instruments. Most metallic objects, however, are not compatible with MRI scanners and can cause problems ranging from image artifacts to dangerous heating and violent displacement. Embodiments of the present invention do not require metal parts. For example polymer cables may be used for actuation, making it easily MRI-compatible by guiding these cables via one (or multiple) pulley(s) out of the MRI scanner bore to the actuation units. MRI machines can integrate systems of the present invention as a built-in feature, allowing streamline conversion of any diagnostic MRI into to surgical therapy under direct MRI guidance. For example a renal/hepatic/prostate tumour may be detected on a screening MRI. An MRI with a system according to the invention integrated into it could allow the taking of biopsies or immediate full tumour surgical removal.
- Cost-effective and reduced footprint. Low-cost and off-the-shelf hardware should represent a competitive price-tag advantage against current systems. Reduced footprint in operating rooms allows quick setup and optimisation of surgical schedules. Both these advantages lower the threshold for administrators and healthcare providers to purchase surgical robotic systems.

The invention claimed is:

1. A medical apparatus comprising: an instrument channel configured to be inserted into the body of a patient to enable a medical instrument to be inserted through the instrument channel into the body of the patient; at least one support structure configured to be located around the body of the patient; a plurality of guide ports each configured to be inserted into the body of the patient; a plurality of control linkages each of which is at least partly supported on the at least one support structure; an instrument holder configured to be inserted through the instrument channel into the body of the patient wherein each of the control linkages is configured to be connected to the instrument holder thereby to manipulate the medical instrument; and a plurality of control actuators; wherein each of the control linkages is configured to extend through one of the guide ports, to be connected to the medical instrument, and to be moved by a respective one of the control actuators thereby to manipulate the medical instrument within the body of the patient.

2. A medical apparatus according to claim 1 further comprising the medical instrument.

3. An apparatus according to claim 1 wherein at least one of the control linkages is a flexible tendon configured to pull the instrument towards the guide port through which it extends.

4. An apparatus according to claim 1 wherein at least one of the control linkages is a rigid rod configured to push and pull the medical instrument.

5. An apparatus according to claim 4 wherein one of the actuators is configured to support the rigid rod and comprises a remote centre of motion actuator.

6. An apparatus according to claim 1 wherein each of the guide ports comprises a rigid tubular member.

7. An apparatus according to claim 6 wherein each of the guide ports is supported by a remote centre of motion actuator.

8. An apparatus according to claim 7 wherein the support structure defines an operating volume in which the body of the patient can be located, and the remote centre of motion actuator has a centre of motion which is within the operating volume.

9. An apparatus according to claim 1 further comprising at least one further control linkage at least partially supported on the instrument channel.

10. An apparatus according to claim 9 wherein the instrument channel comprises an instrument insertion arm which is articulated and comprises a main section, an end section and an articulation joint, wherein the end section is connected to the main section by the articulation joint which allows it to articulate relative to the main section.

11. An apparatus according to claim 10 further comprising an articulation linkage configured to control the angle of articulation of the end section and an actuator configured to actuate the articulation linkage, and the at least one further control linkage is at least partly supported on the end section.

12. An apparatus according to claim 1 further comprising an instrument insertion port through which the instrument channel is configured to be inserted into the body of the patient.

13. An apparatus according to claim 12 further comprising at least one further control linkage at least partially supported on the instrument insertion port.

14. A medical apparatus 1 comprising: an instrument channel configured to be inserted into the body of a patient to enable a medical instrument to be inserted through the instrument channel into the body of the patient; at least one support structure configured to be located around the body of the patient; a plurality of guide ports each configured to be inserted into the body of the patient; a plurality of control linkages each of which is at least partly supported on the at least one support structure; and a plurality of control actuators; wherein each of the control linkages is configured to extend through one of the guide ports, to be connected to the medical instrument, and to be moved by a respective one of the control actuators thereby to manipulate the medical instrument within the body of the patient, wherein at least one of the control linkages is configured to transmit a force to the instrument, and the apparatus further comprises a force sensor configured to measure the force, the apparatus further comprising an input member configured to be manipulated by a surgeon, a feedback actuator configured to apply a force to the input member, and controller configured to control the control actuators in response to movement of the input member, and to control the feedback actuator to provide a feedback force to the input member which is dependent on the force sensed by the force sensor.

15. An apparatus according to claim 1 wherein the at least one support structure comprises a single support structure configured to extend around the body of the patient and to support each of the control linkages.

16. An apparatus according to claim 1 wherein the at least one support structure comprises a plurality of support structures configured to be located around the body of the patient and each configured to support one of the control linkages.

17. A apparatus comprising: an instrument channel configured to be inserted into the body of a patient to enable a medical instrument to be inserted through the instrument channel into the body of the patient; at least one support structure configured to be located around the body of the patient; a plurality of guide ports each configured to be inserted into the body of the patient; a plurality of control linkages each of which is at least partly supported on the at least one support structure; and a plurality of control actuators; wherein each of the control linkages is configured to extend through one of the guide ports, to be connected to the medical instrument, and to be moved by a respective one of the control actuators thereby to manipulate the medical instrument within the body of the patient, wherein the at least one support structure is configured to be attached to the body of the subject, and the at least one support structure is configured to be connected to the body of the subject by adhesive, or stitching, or suction; the apparatus further comprising a motion sensor configured to sense movement of the body, and a controller configured to receive signals from the motion sensor and to control the control actuators so as to compensate for the movement of the body and/or the actutators.

18. A medical apparatus comprising: an instrument channel arranged to be inserted into the body of a patient to enable a medical instrument to be inserted through the instrument channel into the body of the patient; at least one support structure arranged to be located around the body of the patient; a plurality of guide ports each arranged to be inserted into the body of the patient remotely from the instrument channel; a plurality of control linkages each of which is at least partly supported on the at least one support structure; and a plurality of control actuators; wherein each of the control linkages is arranged to extend through one of the guide ports, to be connected to the medical instrument, and to be moved by a respective one of the control actuators thereby to manipulate the medical instrument within the body of the patient, wherein the apparatus further comprises at least one further control linkage at least partially supported on the instrument channel, wherein the instrument channel comprises an instrument insertion arm which is articulated and comprises a main section, and an end section which is connected to the main section by an articulation joint allowing it to articulate relative to the main section, and an articulation linkage arranged to control the angle of articulation of the end section and an actuator arranged to actuate the articulation linkage.

* * * * *